US00RE38721E

(19) United States
(12) Reissued Patent
Jensen et al.

(10) Patent Number: US RE38,721 E
(45) Date of Reissued Patent: *Apr. 12, 2005

(54) POLYMERIZABLE ISOLATION BARRIERS WITH REDUCED POLYMERIZATION STRENGTH AND METHODS FOR FORMING AND USING SUCH BARRIERS

(75) Inventors: Steven D. Jensen, South Jordan, UT (US); Dan E. Fischer, Sandy, UT (US)

(73) Assignee: Ultradent Products, Inc., South Jordan, UT (US)

( * ) Notice: This patent is subject to a terminal disclaimer.

(21) Appl. No.: 10/027,707

(22) Filed: Dec. 19, 2001

Related U.S. Patent Documents

Reissue of:
(64) Patent No.: 6,305,936
Issued: Oct. 23, 2001
Appl. No.: 08/802,674
Filed: Feb. 19, 1997

(51) Int. Cl.[7] ..... A61C 5/14
(52) U.S. Cl. ..... 433/136; 433/217.1
(58) Field of Search ..... 433/136, 138, 433/140, 217.1, 229, 215, 29

(56) References Cited

U.S. PATENT DOCUMENTS

| | | | | |
|---|---|---|---|---|
| 4,303,066 A | * | 12/1981 | D'Andrea | 212/300 |
| 4,531,914 A | | 7/1985 | Spinello | |
| 4,846,165 A | * | 7/1989 | Hare et al. | 228/156 |
| 5,213,498 A | | 5/1993 | Pelerin | |
| 5,296,513 A | * | 3/1994 | Ige et al. | 523/115 |
| 5,410,016 A | * | 4/1995 | Hubbell et al. | 528/354 |
| 5,472,991 A | | 12/1995 | Schmitt et al. | |
| 5,534,562 A | | 7/1996 | Jensen et al. | |
| 5,573,934 A | * | 11/1996 | Hubbell et al. | 435/177 |
| 5,587,406 A | | 12/1996 | Yamamoto et al. | |
| 5,661,222 A | | 8/1997 | Hare | |
| 5,676,543 A | | 10/1997 | Dragan | |
| 5,900,245 A | * | 5/1999 | Sawhney et al. | 424/464 |

OTHER PUBLICATIONS

Orbabase® Plain (Product), Colgate–Hoyt Laboratories, Canton, MA.
Orbabase®–B Benzocaine (Product), Colgate–Hoyt Laboratories, Canton, MA.

* cited by examiner

*Primary Examiner*—Kevin Shaver
*Assistant Examiner*—Melba Bumgarner
(74) *Attorney, Agent, or Firm*—Workman Nydegger

(57) ABSTRACT

The polymerizable dental isolation barrier has a monomer and an initiator. The barrier composition has at least one additive including a polymer strength reducer, a wet tissue adherence accentuator, and a reflective material. The polymer strength reducer is an organic compound that prevents complete polymerization. The tissue adherence accentuator enables the barrier to adhere to a dental substrate even after polymerization. The reflective material lowers the reaction rate and lowers the production of excess heat to reduce patient discomfort and to avoid tissue damage.

89 Claims, 2 Drawing Sheets

POLYMERIZABLE ISOLATION BARRIERS WITH REDUCED POLYMERIZATION STRENGTH AND METHODS FOR FORMING AND USING SUCH BARRIERS

Matter enclosed in heavy brackets [ ] appears in the original patent but forms no part of this reissue specification; matter printed in italics indicates the additions made by reissue.

BACKGROUND OF THE INVENTION

1. The Field of the Invention

The present invention relates to compositions and methods for isolating dental tissue for treatment thereupon. In particular, the present invention relates to polymerizable isolation barrier compositions and methods of using the same for isolating tooth surfaces. The polymerizable barrier compositions of the present invention may include constituents that enable the compositions to adhere to wet, dry, soft or hard oral tissues; to minimize injury risks due to heat from polymerization and/or light radiant energy from subsequent treatment(s); and that enable the barriers to be easily removed.

2. The Relevant Technology

Several dental procedures exist that use treatment compositions in the mouth that could be harmful and damaging to soft tissue. Harmful treatment compositions must be kept away from soft tissue such as the gums during such treatment procedures. There are other dental procedures that require a substantially dry tooth that must be maintained in a dry condition during a lengthy dental procedure to avoid damage.

In general, contact between a treatment composition and the cheeks and tongue of a patient can be minimized through the use of cotton rolls, absorbent isolators, rubber dams, rubber dam caulking or other conventional isolation techniques. The gums, adjacent dentin and surrounding sulcular tissues however are harder to protect from the treatment composition(s) due to their close proximity to the surfaces being treated and because the treatment composition is sometimes a freely flowable aqueous solution.

Although it is possible to incorporate some treatment compositions within a gel in order to inhibit the unwanted flow of the treatment composition from the desired treatment area, they generally must have a low enough viscosity to flow into the tiny crevices and other irregularities of the surface of the tooth being treated. Hence, it is generally impractical to have a treatment composition that is so viscous that it is not at least partially flowable.

In addition to adjusting the flow characteristics, the concentration of the treatment composition can be modified to reduce the damage caused by inadvertent contact with surrounding sulcus and gum tissues. However, significantly reducing the concentration of a treatment composition also reduces its ability to treat the tooth, thereby increasing the time in which the treatment composition must remain in contact with the surface being treated. In general, treatment compositions strong enough to adequately treat teeth may also damage and irritate surrounding soft gum tissues.

Rubber dam technology was developed as a means of isolating a tooth for treatment and also for protecting the vulnerable soft tissue. FIG. 1 illustrates the installation of a rubber dam 10. It can be seen that rubber dam 10 has been placed over the teeth 14 and then rubber dam 10 is fitted with a dental instrument 16 by pushing rubber dam 10 up to the gum line 12. This procedure must be carried out on each tooth. Rubber dams, however, have several disadvantages. One disadvantage is that rubber dams can be difficult to install. Rubber dams have a hole-punched perimeter shape that may or may not isolate soft tissue next to the tooth because the tooth perimeter shape might have concavities. For example, where a tooth forms an unusual groove or concavity, a hole-punched rubber dam may leave an exposed space through which treatment compositions could leak that could harm soft tissue. If the seal created by a rubber dam is faulty, soft tissue is exposed and likely to be damaged by the treatment composition.

Another disadvantage to rubber dams is that they are prone to tearing once placed over the tooth. If the rubber dam begins to tear in the middle of a dental procedure, the procedure must be aborted and a new rubber dam installed. This is time consuming and the new rubber dam may likewise tear at or near the same point of the treatment that the original rubber dam began to tear. Additionally, when the rubber dam tears during a procedure, it may be too late to prevent the treatment compositions from contacting the soft tissue and therefore too late to prevent soft tissue damage.

Another disadvantage to rubber dams is that they often cause patient discomfort. FIG. 2 illustrates installation of a rubber dam 10 with rubber dam clamps 22 and a frame 20 that covers the labia 24 and the tongue 26. When, for example, a labial surface of a tooth is the only surface that needs to be isolated, rubber dam 10 may cover more than the teeth.

Additionally, where an intense dental curing or laser light is being used, heat buildup incidental to use of the light may cause patient discomfort due to heating of the rubber dam. Intense heating of the soft tissue will necessitate intermittent use of the dental light, a practice that slows the clinician in his procedure.

One attempt to overcome the problems associated with rubber dams provided a blue flowable resin that can be applied onto a dental substrate and then be polymerized. Due to the color of the resin, it absorbs light energy which resulting increases the risk of injury to soft tissue in contact with the resin. Additionally, the resin is hydrophobic which significantly hinders its ability to adhere well to dental tissues. Another significant problem with this resin is that it is too strong and consequently the polymerized resin is very difficult to remove. Difficulties related to excessive strength are only exacerbated by application of the resin onto dental surfaces such as wide open embrasures and undercuts. For example, open embrasures are typically filled from both sides which results in the embrasures being completely filled and solidly anchored. After polymerization, it is very difficult to remove the resin and may require prying instruments or even high speed drills. Similarly, undercuts present a problem when resin becomes lodged into the openings or crevices and it may then necessary be to remove the resin with dental tools which the require the use of some force such as prying instruments or excavating tools.

In light of the foregoing, it would be a significant advancement in the art to provide isolation barrier compositions and methods for protecting sulcular and gum tissues surrounding a tooth being treated from intense cumulative heat buildup in order to avoid patient discomfort and to expedite dental treatments that use a curing or laser light It would also be a significant advancement in the art to provide isolation barrier compositions and methods for protecting sulcular and gum tissues surrounding a tooth being treated that can be easily removed following a dental procedure.

It would be a further advancement in the art to provide compositions and methods that result in a quickly and easily applied barrier to maintain a treatment composition within the area of the tooth that is desired to be treated.

Another advancement in the art would be to provide compositions for an isolation barrier material that, upon application to the dental substrate and polymerization, are sufficiently weakened to facilitate its removal in discrete, approximately tooth-sized segments or larger with a tweezers-like instrument from the dental substrate after use in a dental procedure.

Another advancement in the art would be to provide compositions for an isolation barrier material that, upon application to the dental substrate and polymerization, are resistant to deformation at the external surface of the barrier due to incidental touching but that remain adherent to the dental substrate at the internal surface of the barrier.

Another advancement in the art would be to provide a composition for an isolation barrier material that, upon application to the dental substrate and polymerization, is of a generally small size and conducive to a customized fit that avoids inducing patient discomfort.

Such polymerizable isolation barrier compositions and methods for using them are disclosed and claimed herein.

SUMMARY AND OBJECTS OF THE INVENTION

It is an object of the present invention to provide isolation barrier compositions and methods for protecting tissues surrounding a tooth and that can be easily removed following a dental procedure.

It is a further object of the present invention to provide compositions and methods that result in a quickly and easily applied barrier to maintain treatment composition within the area of the tooth that is desired to be treated.

Another object of the present invention is to provide compositions for an isolation barrier material that, upon application to the dental substrate and polymerization, are sufficiently weakened to facilitate their removal in discrete, approximately tooth-sized segments or larger with a tweezers-like instrument from the dental substrate after use in a dental procedure and even easily break lose from undercuts or when located between a large embrasure.

Another object of the present invention is to provide compositions for an isolation barrier material that, upon application to the dental substrate and polymerization, are resistant to deformation at the external surface of the barrier due to incidental touching but that remain adherent to the dental substrate at the internal surface of the barrier.

Another object of the present invention is to provide compositions for an isolation barrier material that, upon application to the dental substrate and polymerization, are configured to decrease the polymerization reaction rate and thereby reduce patient discomfort and thermal tissue damage due to substantial heat production during polymerization.

Various compounds were found to assist in formulation of a polymerizable isolation barrier for several types of dental procedures. These compounds are advantageously added together in whole or in partial combinations to achieve specific advantages over the prior art.

The isolation barrier of the present invention is made polymerizable by providing at least one monomer in the inventive composition. The monomer is preferably of substantially low toxicity to humans. The monomer can be a single monomer or a selection of monomers depending upon the specific application.

One advantage to using preferred monomers is that a cohesive isolation barrier may be fashioned in the mouth and the need for the traditional rubber dam is eliminated. As such, the clinician is not concerned with punching, fitting, repairing, and sealing a rubber dam, rather, with the inventive isolation barrier, the polymerizable isolation barrier is applied to seal soft tissue and isolate hard tissue for a desired procedure, and is removed in integral, tooth-sized segments or larger after completion of the dental procedure.

A curing agent is provided to induce the monomer to cross link upon exposure to adequate light radiant energy. The curing agent is preferably of substantially low toxicity to humans. Curing agents may also be selected to be complementary to other ingredients for a selected dental procedure. Optional additives are preferred in formulating curing agents depending upon the specific application of the polymerizable isolation barrier.

During polymerization, there are several variables to monitor. Heat is usually generated during polymerization. A significant increase in temperature during polymerization can cause discomfort to the patient or can be sufficient to also cause burning of oral tissue. To control heat production, an organic compound is preferred that will provide a compositional quality of preventing complete polymerization of the isolation barrier material, thus, the total exothermic heat potential for a given amount of monomer will be reduced during polymerization. In addition to preventing unwanted excess heat of reaction, it was found that certain organic compounds cause the isolation barrier material to become significantly weakened or brittle compared to a barrier material without such organic compounds. A weakened isolation barrier has the advantage of easy removal after completion of the dental procedure. The clinician can take hold of the polymerized isolation barrier with an instrument like tweezers and remove it in discrete segments that are about the size of a tooth or larger. The advantage is that, where a principally hydrophobic isolation barrier is required for a given dental procedure, removal after the procedure takes only one removal step or at most a few removal steps and if any smaller portions crumble, they are easily rinsed away after being dislodged.

During polymerization, it would be advantageous that the interior surface of the inventive isolation barrier will slightly adhere to wet or dry, hard or soft tissue (henceforth "tissue"). The term "slightly adhere," refers to adherence of the isolation barrier to tissue that, upon removal, will not substantially remove epithelial tissue of the gums in a way that causes discomfort to the dental patient. As a feature of the present invention, it was found that when an adherence accentuator is added, the isolation barrier material will adhere better to tissue before, during, and after polymerization.

When the barrier is utilized in a dental procedure such as bleaching with a peroxide composition that would harm tissue, a preferred procedure is to apply the isolation barrier composition and begin to polymerize with a dental curing light. Later, as the dental curing light is also used to activate the peroxide bleaching composition, polymerization may continue. With preferred tissue adherence accentuators, the isolation barrier composition continues to adhere to wetted tissue even when the monomer becomes substantially polymerized. An advantage of this feature of the invention is that a substantially conformal isolation barrier can be laid up against the tooth to isolate it and the barrier will adhere adequately to tissue during a time period for standard isolation treatment procedures.

Another method of lowering harmful amounts of excess heat released during polymerization or during a subsequent dental procedure is to reflect some of the light radiant energy of the dental light away from the isolation barrier composition. Dental curing lights and laser treatment lights typically come with only intense light radiation settings. These intense light radiation settings are very desirable in some dental applications such as in peroxide teeth bleaching. It was found that the addition of reflective materials reflects some portion of the dental light thereby reducing heating of the isolation barrier during a dental procedure and minimizing harmful conductive or radiant heat transfer to gums or other soft tissues. Thus, the composition absorbs less light radiant energy, the isolation barrier is less energized than would be otherwise, and the underlying gum tissue is not subjected to undue heating during a dental procedure.

The inventive polymerizable isolation barrier material is preferably made in a paste or gel form that is [Theologically] *rheologically* able to be expressed from a dental syringe. The components of the isolation barrier material form either an emulsion or a solution depending upon selection of a preferred application.

The inventive polymerizable isolation barrier material is also preferably made in a roll or tape form of a curable putty. The roll or tape is unrolled, cut into a strip to a desired length, placed onto the gums, pressed substantially conformably into place, for example with finger pressure, carved to isolate hard tissue, and then cured with light radiant energy. The components of this isolation barrier material form either an emulsion, a dispersion, a suspension, a solution, etc. depending upon selection of a preferred application.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The polymerizable isolation barriers are useful for many types of dental procedures. The polymerizable isolation barrier compositions comprise at least a monomer, a curing agent, and at least one other constituent. The other constituents include polymerization strength reducers, tissue adherence accentuators and reflective materials. The compositions can be utilized with any light radiant energy which includes the full electromagnetic spectrum.

The polymerization strength reducers prevent the polymerizable composition from becoming difficult to remove. The tissue adherence accentuators ensure adequate adhesion to any dental substrate. The reflective materials reflect light radiant energy. By reflecting light radiant energy, the heat produced by polymerization is maintained to a desirable level and harmful conductive or radiant heat transferred to gums or other soft tissues during a subsequent procedure is minimized. The combinations achieve specific advantages over the prior art.

A. Monomers

The isolation barrier of the present invention is made polymerizable by providing at least one monomer in the inventive composition. The monomer is preferably of substantially low toxicity to humans. The monomer can be a single monomer or a selection of monomers depending upon the specific application. For example, when performing a dental procedure involving acid etching, it is preferred to select a monomer or combination thereof that, when polymerized, is resistant to acid, thus, the isolation barrier will hold a seal against tissue to protect it from the acid.

One advantage to using the polymerizable isolation barrier is that a cohesive isolation barrier may be fashioned in situ in the mouth and the need for the traditional rubber dam is eliminated. As such, the clinician is not concerned with punching, fitting, repairing, and sealing a rubber dam, rather, with the inventive isolation barrier, the isolation barrier is applied to seal tissue and isolate hard tissue for a desired procedure, is polymerized, and is removed in integral tooth-sized segments or larger after completion of the dental procedure. The clinician can remove the barrier by any means. However, the composition enables a clinician to take hold of the polymerized isolation barrier by hand and easily remove it as an integral unit or in discrete segments, or a dental instrument like tweezers can be used for easy removal.

Figure 1:
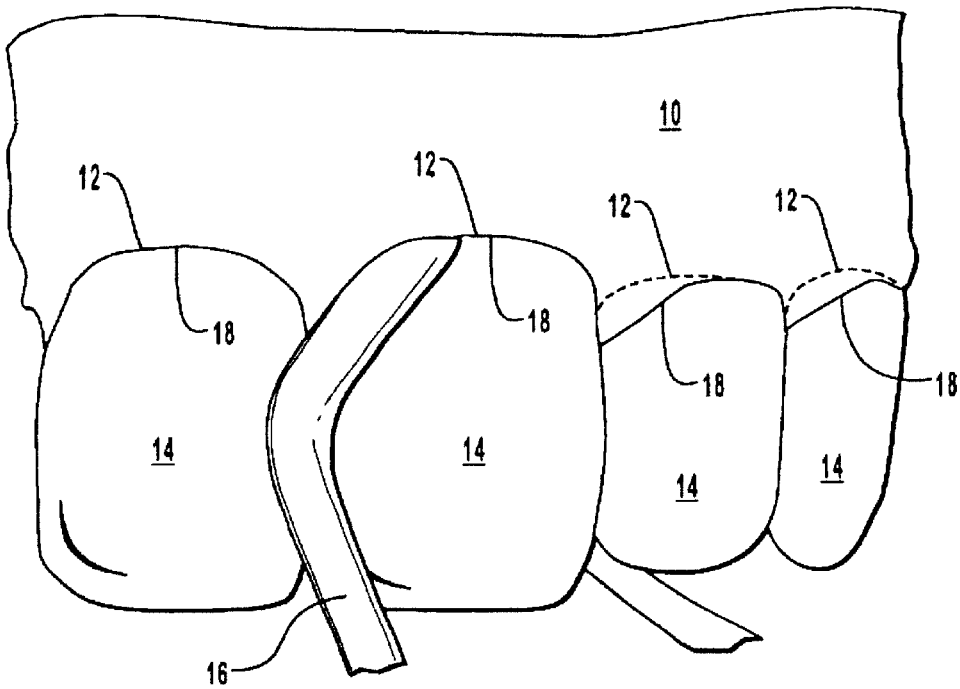
FIG. 1 (PRIOR ART)
FIG. 1 is a prior art elevational front view of teeth and gums that are being isolated and protected, respectively in preparation for a dental procedure that requires isolating the teeth for the procedure while protecting tissue including gums from the treatment composition, and in which it can be seen that a rubber dam is the medium to protect the tissue by which it is being fitted to the tooth-gum juncture by a dental instrument.
Figure 2:
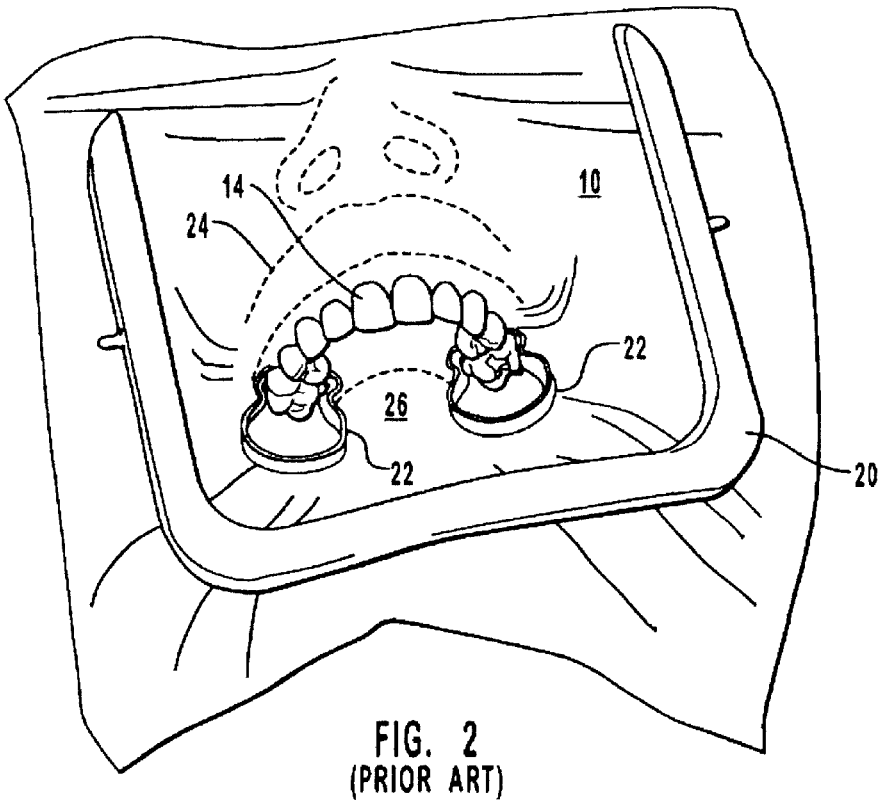
FIG. 2 (PRIOR ART)
FIG. 2 is a prior art elevational view of a patient with a rubber dam installed that includes a rubber dam frame and rubber dam clamps that are secured to a large molar.
Figure 3:
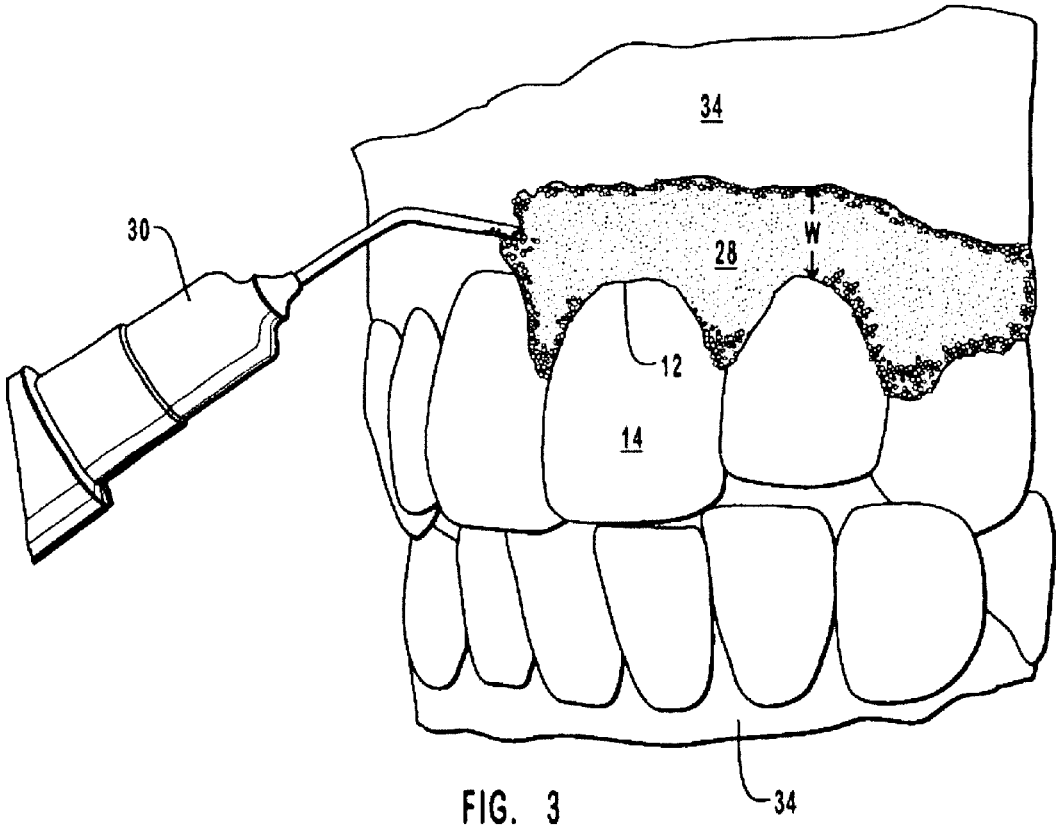
FIG. 3 is an elevational front view of a patient during installation of the inventive isolation barrier, in which the isolation barrier is being expressed through a syringe substantially conformable to the tooth-gum interface in preparation for polymerization by light radiant energy.

The size of the discrete segments is generally about one-half the area that the isolation barrier is isolating. For example, as illustrated in FIG. 3, if the clinician were to stop applying the inventive isolation barrier at the point illustrated therein, the size of the discrete segments would generally be about one-half the length as applied. Another example is when the whole arch is being isolated, it is preferable that the discrete segments are at least about one-fourth the length of the arch, more preferably at least about one-half the length of the arch, and most preferably the isolation barrier will be removed as an integral unit.

Examples of suitable monomers include alkylmethacrylates, alklyhydroxymethacrylates, and alkylaminomethacrylates and derivatives thereof. The alkylmethacrylates include triethylene glycol dimethacrylate, polyethylene glycol (PEG) dimethacrylate (all molecular weights), butane di-ol dimethacrylate, and equivalents. The alkylhydroxymethacrylates include 2-hydroxy ethyl methacrylate, glycerol dimethacrylate, bis-GMA, and equivalents. The alkylaminomethacrylates include urethane dimethacrylate and equivalents. The monomers of the present invention are provided in a concentration range from about 50 to about 99 percent, preferably from about 60 to about 95 percent, and most preferably from about 70 to about 90 percent by weight of the composition. The preferred methacrylates include alkylmethacrylates. The more preferred methacrylate is triethylene glycol dimethacrylate. In addition to the above methacrylates, other monomers are within the contemplation of the present invention and can be found by routine experimentation by reading the disclosure and practicing the invention.

B. Curing Agents

Curing agents were found to be useful, and depending upon the specific dental procedure, were preferred with or without certain organic amine additives.

A curing agent is provided to induce the monomer to cross link upon exposure to adequate light radiant energy. The curing agent is preferably of substantially low toxicity to humans. Curing agents may also be selected to be complementary to other ingredients for a selected dental procedure. Curing agents include photoinitiators and amine additives as needed.

Examples of photoinitiators include camphorquinone; benzoin methyl ether; 2-hydroxy-2-methyl-1-phenyl-1-propanone; diphenyl 2,4,6-trimethylbenzoyl phosphine oxide; benzoin ethyl ether; benzophenone; 9,10-anthraquinone, and equivalents.

Optional additives such as amine additives are preferred in formulating curing agents to assist the curing agents depending upon the specific application of the polymerizable isolation barrier. Examples of amine additives include dimethyl amino ethyl methacrylate; tri ethyl amine; 2-dimethylamino ethanol; diethyl amino ethyl methacrylate; trihexyl amine; N,N-dimethyl-p-toluidine; N-methylethanolamine, and equivalents.

The curing agents of the present invention are provided in a concentration range from about 0.01 to about 2 percent, preferably from about 0.1 to about 1 percent, more preferably from about 0.2 to about 0.8 percent, and most preferably about 0.3 percent by weight of the composition. The preferred curing agent includes 2-hydroxy-2-methyl-1-phenyl-1-propanone and diphenyl 2,4,6-trimethylbenzoyl phosphine oxide. In addition to the above curing agents, other curing agents are within the contemplation of the present invention and can be found by routine experimentation by reading the disclosure and practicing the invention.

C. Polymerization Strength Reducers

During polymerization, there are several variables to consider. Heat is usually generated during polymerization due to the exothermic nature of polymerization. A significant increase in temperature during polymerization can cause discomfort to the patient or can be sufficient to also cause burning.

An organic compound is preferred that has the capability to substantially decrease or minimize the degree of polymerization of the isolation barrier material compared to a barrier material without such an organic compound. Thus, the total exothermic heat potential for a given amount of monomer will be reduced during polymerization.

In addition to preventing unwanted excess heat of reaction, it was found that certain organic compounds cause the isolation barrier material to become weakened. A weakened isolation barrier has the advantage of easy removal after completion of the dental procedure. The clinician can take hold of the polymerized isolation barrier by hand or with an instrument like tweezers and remove it in discrete segments or as integral unit. The size of the discrete segments is generally about one-half the area that the isolation barrier is isolating. For example, when the whole arch is being isolated, it is preferable that the discrete segments are at least about one-fourth the length of the arch, more preferable at least about one-half the length of the arch, and most preferably the isolation barrier will be removed as an integral unit. The advantage is that, where a hydrophobic isolation barrier is required for a given dental procedure, removal after the procedure takes only one or a few removal steps and any small portions that may crumble are easily rinsed away after being dislodged.

Examples of suitable polymerization strength reducers include oils such as mineral oils. Other suitable examples include alcohols such as cetyl alcohol, steryl alcohol, derivatives thereof, and equivalents. Yet other suitable examples include polyols such as polyethylene glycols, polypropylene glycols, propylene glycol, derivatives thereof, and equivalents. The polymerization strength reducers of the present invention are provided in a concentration range, when included, from about 1 to about 30 percent, preferably from about 5 to about 20 percent, more preferably from about 10 to about 15 percent, and most preferably about 12 percent by weight of the composition. Of the polymerization strength reducers, the preferred includes cetyl alcohol.

D. Tissue Adherence Accentuators

During polymerization of the isolation barrier and during treatment, it is desirable that the isolation barrier adhere between an interior surface of the inventive isolation barrier and wetted tissue. As a feature of the present invention, it was found that when an adherence accentuator is added, the isolation barrier material will adhere better to tissue before, during, and after polymerization. An inner surface of the isolation barrier is one that interfaces with the dental substrate.

When the isolation barrier is utilized as part of a dental procedure involving teeth bleaching with a peroxide composition that would harm tissue, it is preferable to apply the isolation barrier composition and begin to polymerize with a dental light. After the barrier is positioned and polymerized, the dental light is used to activate the peroxide bleaching composition which also may cause continued polymerization of the isolation barrier. With preferred tissue adherence accentuators, the isolation barrier composition continues to gently adhere to wetted tissue even when the monomer becomes substantially polymerized. An advantage of this feature of the invention is that a substantially conformal isolation barrier can be laid up against the tooth to isolate it and it will adhere adequately to tissues during a time period for standard isolation treatment procedures.

Examples of tissue adherence accentuators include gums such as xanthan gum, guar gum, tragacanth gum, their derivatives, and equivalents. Other examples include cellulose materials such as ethyl cellulose, hydroxypropyl methyl cellulose, their derivatives, and equivalents. Yet other examples include polymers such as carboxy poly methylene, polysiloxanes, water-soluble polyethylene oxide polymers, derivatives and equivalents. The water-soluble polyethylene oxides preferably have molecular weights of around 100,000 or more even up to several million. The preferred water-soluble polyethylene oxide polymer is sold as Polyox™ by Union Carbide. Additionally, high molecular weight polyols can function as tissue adherence accentuators such as polypropylene glycols and polyethylene glycols having a molecular weight of at least 600. The tissue adherence accentuators of the present invention, when used, are supplied to the inventive composition in a concentration range from about 0.01% to about 9%, preferably from about 0.03% to about 5%, more preferably from about 0.05% to about 3%, and most preferably about 0.1% by weight of the composition. The preferred tissue adherence accentuator is xanthan gum.

E. Reflective Materials

Another method of lowering harmful amounts of excess heat released during polymerization is to reflect some of the light radiant energy of the dental light away from the isolation barrier composition. Dental curing lights and laser treatment lights typically come with only intense light radiation settings, which is desirable in certain applications such as peroxide teeth bleaching. It was found that the addition of reflective materials causes a portion of the dental light to be reflected thereby reducing heating of the isolation barrier during polymerization, particularly when polymerized with a light at an intense light radiation setting, and during a subsequent dental procedure such as bleaching. Thus, the composition absorbs less light radiant energy, the isolation barrier is less energized than would be otherwise, the underlying gum tissue is not subjected to undue heating during a dental procedure that uses a curing or laser light and light is even reflected away from the underlying gums or other protected tissue.

Examples of reflective materials include metals such as gold flake, aluminum flake, titanium flake, and equivalents. Other examples include metal oxides such as aluminum oxide, titanium dioxide, precipitated silica, ceria, thoria and equivalents. Yet other examples include micas and equivalents. The reflective materials of the present invention, when included, are provided in a concentration range from about 1 to about 50 percent, preferably from about 2 to about 30 percent, more preferably from about 3 to about 20 percent, and most preferably about 15 percent. The preferred reflective material comprises micas.

F. General Properties

It is advantageous to combine various aspects of the present invention for preferred applications. For example, a peroxide gel may be the treatment composition and light radiant energy will be used both during polymerization of the compositions of the present invention and later during peroxide bleaching material. In such a case, the clinician may select a composition that includes polymerization strength reducers, tissue adherence accentuators, and reflecting materials. Thus, such a composition will achieve a weakened isolation barrier for easy removal and for resistance to incidental touching during the dental procedure, it will assure that the isolation barrier sufficiently remains in place to adequately seal off the soft tissue while the bleachant is on the tooth, and reflects intense light energy during a treatment procedure to protect the underlying gums from undue heating.

Alternatively, an application might be required where the tooth is to be isolated for dryness purposes. In such a case, the clinician may select a composition that includes polymerization strength reducers and tissue adherence accentuators. Thus, such a composition will achieve a weakened isolation barrier for easy removal yet adequate resistance to incidental touching during the dental procedure, and the composition will remain sufficiently in place against tissue during the procedure.

The method of making the polymerizable isolation barrier is carried out by providing at least one monomer; providing at least one curing agent for curing the at least one monomer; and by providing at least one of three preferred additives that include the organic polymerization strength reducer, the tissue adherence accentuator, or the reflective material. The ingredients are blended in a container until homogeneous, and the homogenous mixture is place in a container that is resistant to light energy. The inventive polymerizable isolation barrier material is preferably stored at or below room temperature. The inventive polymerizable isolation barrier material is stable enough to be stored under normal conditions at the operatory until activated by suitable light radiant energy.

G. Methods of Use

The inventive polymerizable isolation barrier material is made in a paste or gel form that is [Theologically] *rheologically* able to be expressed from a dental syringe. The components of the isolation barrier material form either an emulsion or a solution depending upon selection of a preferred application. The inventive polymerizable isolation barrier material is also preferably made in a roll or tape form of a curable putty that is rolled onto the gums, pressed into place, for example with finger pressure, carved to isolate hard tissue, and then cured with light radiant energy. The components of this isolation barrier material form either an emulsion, dispersion, suspension, solution, etc. depending upon selection of a preferred application.

The inventive polymerizable isolation barrier material is applied by any of several methods. FIG. 3 is an elevational oblique view of a patient during installation of the inventive isolation barrier 28, in which isolation barrier 28 is being expressed through a syringe 30 substantially conformably to the tooth-gum interface 32 in preparation for polymerization by light radiant energy. A preferred method of use is to dry the tooth or teeth that are to be treated, retract the labia, and apply the isolation barrier material 28 with syringe 30 conformably at the base of the tooth upon the tissue such as the gums 34. The width W of isolation barrier 28 as it extends across tissue may be selected by the clinician according to the application. For example, where a gel is being used and running of the gel is not likely, the clinician may apply a substantially conformal isolation barrier that touches the teeth and extends onto the gums 34 from about three to about 10 mm from the area to be treated. Larger or smaller isolation barriers may be applied depending upon the specific dental procedure.

Figure 4:
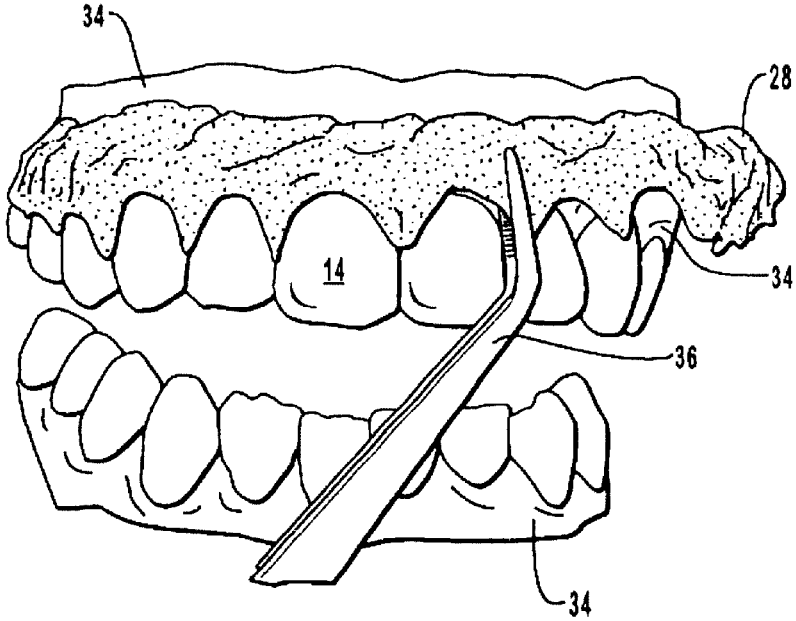
FIG. 4 is an elevational front view of a patient during removal of the inventive isolation barrier after polymerization, in which the isolation barrier is being removed in a discrete segment with a tweezers-like instrument.

Removal of isolation barrier 28 after the dental treatment is accomplished as illustrated in FIG. 4. A tweezers-like instrument 36 may be used to remove isolation barrier 28 by taking hold of isolation barrier 28 and removing it in discrete segments. It can be seen that isolation barrier 28 is lifting away from gums 34 at the area near where instrument 36 has fastened onto isolation barrier 28. The clinician can take hold of polymerized isolation barrier 28 with instrument 36 and remove it in discrete segments. The size of the discrete segments is generally about one-half the area that isolation barrier 28 is isolating. For example, when the whole arch is being isolated, it is preferable that the discrete segments are about one-fourth the length of the arch, more preferably about one-half the length of the arch, and most preferably, as illustrated in FIG. 4, isolation barrier 28 will be removed as an integral unit.

EXAMPLES OF THE PREFERRED EMBODIMENTS

Several examples of the present invention are presented as merely illustrative of some embodiments of the present invention. These examples are not to be construed as limiting the spirit and scope of the invention. The following nine hypothetical examples were produced in furtherance of reducing the present invention to practice. All amounts are given in weight percent.

| Component | Percent by Weight of the Mixture |
|---|---|
| mica | 2.0 |
| xanthan gum | 0.1 |
| curing agents | 0.3 |
| cetyl alcohol | 12.5 |
| precipitated silica | 13.0 |
| triethylene glycol dimethacrylate | 72.1 |

The foregoing example produces an isolation barrier material composition that, upon application to the dental substrate and polymerization, is sufficiently weakened to facilitate its removal in discrete, tooth-sized segments or larger with a tweezers-like instrument from the dental substrate after use in a dental procedure. The barrier material also is resistant to deformation at the external surface of the barrier due to incidental touching but remains adherent to the dental substrate at the internal surface of the barrier. The barrier material also is configured to decrease the polymerization reaction rate and to reflect excessive light radiant energy to thereby resist thermal tissue damage due to substantial heat production during polymerization.

| Component | Percent by Weight of the Mixture |
|---|---|
| mica | 3.0 |
| xanthan gum | 0.3 |
| curing agents | 0.5 |
| PEO dimethacrylate (300) | 96.2 |

The foregoing example produces an isolation barrier material composition that, upon application to the dental substrate and polymerization, is resistant to deformation at the external surface of the barrier due to incidental touching but remains adherent to the dental substrate at the internal surface of the barrier. The barrier material also reflects excessive light radiant energy in order to resist thermal tissue damage due to substantial heat production during polymerization.

| Component | Percent by Weight of the Mixture |
|---|---|
| titanium dioxide | 1.0 |
| guar gum | 0.1 |
| steryl alcohol | 17.0 |
| precipitated silica | 12.0 |
| 2-hydroxy ethyl methacrylate | 69.0 |
| curing agents | 0.9 |

The foregoing example produces an isolation barrier material composition that, upon application to the dental substrate and polymerization, is sufficiently weakened to facilitate its removal in discrete, tooth-sized segments or larger with a tweezers-like instrument from the dental substrate after use in a dental procedure. The barrier material also is resistant to deformation at the external surface of the barrier due to incidental touching but remains adherent to the dental substrate at the internal surface of the barrier. The barrier material also is configured to decrease the polymerization reaction rate and reflect excessive light radiant energy to thereby resist thermal tissue damage due to substantial heat production during polymerization.

| Component | Percent by Weight of the Mixture |
|---|---|
| xanthan gum | 1.0 |
| PEG dimethyacrylate (600) | 98.5 |
| curing agents | 0.5 |

The foregoing example produces an isolation barrier material composition that, upon application to the dental substrate and polymerization, is resistant to deformation at the external surface of the barrier due to incidental touching but remains adherent to the dental substrate at the internal surface of the barrier.

| Component | Percent by Weight of the Mixture |
|---|---|
| cetyl alcohol | 20.0 |
| tri ethylene glycol dimethyacrylate | 79.0 |
| curing agents | 1.0 |

The foregoing example produces an isolation barrier material composition that, upon application to the dental substrate and polymerization, is sufficiently weakened to facilitate its removal in discrete, tooth-sized segments or larger with a tweezers-like instrument from the dental substrate after use in a dental procedure.

| Component | Percent by Weight of the Mixture |
|---|---|
| titanium dioxide | 1.0 |
| mica | 5.0 |
| urethane dimethyacrylate | 93.8 |
| curing agents | 0.2 |

The foregoing example produces an isolation barrier material composition that, upon application to the dental substrate and polymerization, reflects excessive light radiant energy in order to resist thermal tissue damage due to substantial heat production during polymerization.

| Component | Percent by Weight of the Mixture |
|---|---|
| xanthan gum | 0.2 |
| cetyl alcohol | 12.0 |
| curing agents | 0.5 |
| tri ethylene glycol dimethacrylate | 87.3 |

The foregoing example produces an isolation barrier material composition that, upon application to the dental substrate and polymerization, is sufficiently weakened to facilitate its removal in discrete, tooth-sized segments or larger with a tweezers-like instrument from the dental substrate after use in a dental procedure. The barrier material also is resistant to deformation at the external surface of the barrier due to incidental touching but remains adherent to the dental substrate at the internal surface of the barrier. The barrier material is also configured to decrease the polymerization reaction rate and thereby resist thermal tissue damage due to substantial heat production during polymerization.

| Component | Percent by Weight of the Mixture |
|---|---|
| aluminum oxide | 1.0 |
| xanthan gum | 2.0 |
| curing agents | 0.5 |
| glycerol dimethyacrylate | 96.5 |

The foregoing example produces an isolation barrier material composition that, upon application to the dental substrate and polymerization, remains adherent to the dental substrate at the internal surface of the barrier. The barrier material also is configured to decrease the polymerization reaction rate and thereby resist thermal tissue damage due to substantial heat production during polymerization.

| Component | Percent by Weight of the Mixture |
|---|---|
| cetyl alcohol | 12.0 |
| aluminum flake | 3.0 |
| butane di-ol dimethyacrylate | 84.5 |
| curing agents | 0.5 |

The foregoing example produces an isolation barrier material composition that, upon application to the dental substrate and polymerization, is sufficiently weakened to facilitate its removal in discrete, tooth-sized segments or larger with a tweezers-like instrument from the dental substrate after use in a dental procedure. The barrier material also is configured to decrease the polymerization reaction rate and reflect excessive light radiant energy to thereby resist thermal tissue damage due to substantial heat production during polymerization.

The present invention may be embodied in other specific forms without departing from its spirit or essential characteristics. The described embodiments are to be considered in all respects only as illustrated and not restrictive. The scope of the invention is, therefore, indicated by the appended claims and their combination in whole or in part rather than by the foregoing description. All changes that come within the meaning and range of equivalency of the claims are to be embraced within their scope.

What is claimed and desired to be secured by United States Letters Patent is:

1. A polymerizable isolation barrier for isolating a dental substrate to confine a dental treatment composition to an area defined by the isolation barrier, the polymerizable isolation barrier comprising [the] mixture products of:

at least one monomer;

at least one curing agent for curing the at least one monomer; and at least one organic polymerization strength reducer, *different than the at least one monomer,* for reducing strength of the polymerizable isolation barrier.

2. A polymerizable isolation barrier according to claim 1, wherein the at least *one* monomer includes at least one of an alkylmethacrylate, an alkylhydroxymethacrylate, or an alkylaminomethacrylate.

3. A polymerizable isolation barrier according to claim 1, wherein the at least *one* monomer includes at least one of triethylene glycol dimethacrylate, polyethylene glycol dimethacrylate, butane di-ol dimethacrylate, 2-hydroxyethyl methacrylate, glycerol dimethacrylate, bis-GMA, or urethane dimethacrylate.

4. A polymerizable isolation barrier according to claim 1, wherein the at least *one* monomer is included in a concentration from about 50% to about 99% by weight of *the polymerizable isolation* barrier.

5. A polymerizable isolation barrier according to claim 1, wherein the organic polymerization strength reducer includes at least one alcohol.

6. A polymerizable isolation barrier according to claim 1, wherein the organic polymerization strength reducer includes cetyl alcohol.

7. A polymerizable isolation barrier according to claim 1, wherein the organic polymerization strength reducer includes stearyl alcohol.

8. A polymerizable isolation barrier according to claim 1, wherein the organic polymerization strength reducer includes at least one polyol.

9. A polymerizable isolation barrier according to claim 1, wherein the organic polymerization strength reducer includes at least one oil.

10. A polymerizable isolation barrier according to claim 1, wherein the organic polymerization strength reducer is included in a concentration from about 1% to about 30% by weight of *the polymerizable isolation* barrier.

11. A polymerizable isolation barrier according to claim 1, wherein the organic polymerization strength reducer is in sufficient concentration to lower the ability of the *at least one* monomer to polymerize.

12. A polymerizable isolation barrier according to claim 1, wherein the at least one organic polymerization strength reducer is in sufficient concentration to facilitate removal of [the] *a polymerized isolation* barrier from [the] *a* dental substrate by hand or by a dental tool.

13. A method of making a polymerizable isolation barrier for isolating a dental substrate to confine a dental treatment composition to an area defined by the isolation barrier, the method comprising mixing together at least one monomer, at least one curing agent for curing the at least one monomer, and at least one organic polymerization strength reducer, *different than the at least one monomer,* for reducing strength of the polymerizable isolation barrier.

14. A polymerizable isolation barrier according to claim 1, wherein the organic polymerization strength reducer includes at least one polyol selected from the group consisting of polyethylene glycols, polypropylene glycols, and propylene glycol.

15. A polymerizable isolation barrier according to claim 1, wherein the organic polymerization strength reducer includes mineral oil.

16. A polymerizable isolation barrier according to claim 1, further comprising at least one tissue adherence accentuator, *the at least one tissue adherence accentuator comprising at least one component selected from the group consisting of gums, cellulose materials, polyols having a molecular weight of at least about 600, and polymers.*

17. A polymerizable isolation barrier according to claim 16, wherein the at least one tissue adherence accentuator includes at least one gum.

18. A polymerizable isolation barrier according to claim 16, wherein the at least one tissue adherence accentuator includes at least one gum selected from the group consisting of xanthan gum, guar gum, and tragacanth gum.

19. A polymerizable isolation barrier according to claim 16, wherein the at least one tissue adherence accentuator includes at least one cellulose material.

20. A polymerizable isolation barrier according to claim 16, wherein the at least one tissue adherence accentuator includes at least one cellulose material selected from the group consisting of ethyl cellulose and hydroxypropylmethyl cellulose.

21. A polymerizable isolation barrier according to claim 16, wherein the at least one tissue adherence accentuator includes at least one high molecular weight polyol.

22. A polymerizable isolation barrier according to claim 16, wherein the at least one tissue adherence accentuator includes at least one polyol having a molecular weight of at least about 600 and that includes at least one of polyethylene glycol or polypropylene glycol.

23. A polymerizable isolation barrier according to claim 16, wherein the at least one tissue adherence accentuator includes at least one polymer selected from the group consisting of polsiloxanes, carboxypolymethylene, and water-soluble polyethylene oxides.

24. A polymerizable isolation barrier according to claim 16, wherein the at least one tissue adherence accentuator is included in a concentration from about 0.01% to about 9% by weight of the *polymerizable isolation* barrier.

25. A polymerizable isolation barrier according to claim 16, wherein the at least one tissue adherence accentuator is in sufficient concentration to adhere to the dental substrate at a surface of the isolation barrier interfacing with the dental substrate during a dental procedure.

26. A polymerizable isolation barrier according to claim 1, further comprising at least one reflective material for reflecting light radiant energy, *the at least one reflective material comprising at least one component selected from the group consisting of metals, metal oxides, silica, and mica*.

27. A polymerizable isolation barrier according to claim 26, wherein the at least one reflective material includes at least one metal.

28. A polymerizable isolation barrier according to claim 26, wherein the at least one reflective material includes at least one metal selected from the group consisting of gold flake, aluminum flake, and titanium flake.

29. A polymerizable isolation barrier according to claim 26, wherein the at least one reflective material includes at least one metal oxide.

30. A polymerizable isolation barrier according to claim 26, wherein the at least one reflective material includes at least one metal oxide selected from the group consisting of aluminum oxide, titanium dioxide, precipitated silica, ceria, and thoria.

31. A polymerizable isolation barrier according to claim 26, wherein the at least one reflective material includes at least one mica.

32. A polymerizable isolation barrier according to claim 26, wherein the at least one reflective material is included in a concentration from about 1% to about 50% by weight of the *polymerizable isolation* barrier.

33. A polymerizable isolation barrier according to claim 26, wherein the at least one reflective material is in sufficient concentration to decrease a polymerization reaction rate compared to a polymerization reaction rate of [the] *an* isolation barrier material without [a] *the* reflective material.

34. A polymerizable isolation barrier according to claim 26, wherein the at least one reflective material is in sufficient concentration to prevent substantial thermal tissue damage during [a] polymerization of the isolation barrier.

35. A polymerizable isolation barrier for isolating a dental substrate to confine a dental treatment composition to an area defined by the isolation barrier, the polymerizable isolation barrier comprising [the] mixture products of:

at least one monomer;

at least one curing agent for curing the at least one monomer; and at least one organic polymerization strength reducer, *different than the at least one monomer,* for reducing strength of the polymerizable isolation barrier and that includes at least one of an alcohol, a polyol, or an oil.

36. A polymerizable isolation barrier according to claim 35, wherein the at least *one* monomer includes at least one of an alkylmethacrylate, an alkylhydroxymethacrylate, or an alkylaminomethacrylate.

37. A polymerizable isolation barrier according to claim 35, wherein the *at least one organic polymerization strength reducer comprises an* alcohol *that* includes at least one of cetyl alcohol or stearyl alcohol.

38. A polymerizable isolation barrier according to claim 35, wherein the *at least one organic polymerization strength reducer comprises a* polyol *that* includes at least one of a polyethylene glycol, a polypropylene glycol, or propylene glycol.

39. A polymerizable isolation barrier according to claim 35, wherein the *at least one organic polymerization strength reducer comprises an* oil *that* includes mineral oil.

40. A polymerizable isolation barrier according to claim 35, wherein the *at least one* organic polymerization strength reducer is included in a concentration from about 1% to about 30% by weight of *the polymerizable isolation* barrier.

41. A polymerizable isolation barrier according to claim 35, wherein the *at least one* organic polymerization strength reducer is in sufficient concentration to lower the ability of the *at least one* monomer to polymerize.

42. A polymerizable isolation barrier according to claim 35, wherein the at least one organic polymerization strength reducer is in sufficient concentration to facilitate removal of [the] *a polymerized isolation* barrier from [the] *a* dental substrate by hand or by a dental tool.

43. A polymerizable isolation barrier according to claim 35, further comprising at least one tissue adherence accentuator.

44. A polymerizable isolation barrier according to claim 35, further comprising at least one reflective material for reflecting light radiant energy.

45. A polymerizable isolation barrier for isolating a dental substrate to confine a dental treatment composition to an area defined by the isolation barrier, the polymerizable isolation barrier comprising [the] mixture products of:

at least one monomer;

at least one curing agent for curing the at least one monomer; and at least one organic polymerization strength reducer, *different than the at least one monomer,* for reducing strength of the polymerizable isolation barrier and that includes at least one of cetyl alcohol, stearyl alcohol, a polyethylene glycol, a polypropylene glycol, propylene glycol, or mineral oil.

46. A polymerizable isolation barrier according to claim 45, wherein the at least *one* monomer includes at least one of an alkylmethacrylate, an alkylhydroxymethacrylate, or an alkylaminomethacrylate.

47. A polymerizable isolation barrier according to claim 45, wherein the organic polymerization strength reducer is included in a concentration from about 1% to about 30% by weight of *the polymerizable isolation* barrier.

48. A polymerizable isolation barrier according to claim 45, wherein the organic polymerization strength reducer is in sufficient concentration to lower the ability of the *at least one* monomer to polymerize.

49. A polymerizable isolation barrier according to claim 45, wherein the at least one organic polymerization strength reducer is in sufficient concentration to facilitate removal of [the] *a polymerized isolation* barrier from [the] *a* dental substrate by hand or by a dental tool.

50. A polymerizable isolation barrier according to claim 45, further comprising at least one tissue adherence accentuator.

51. A polymerizable isolation barrier according to claim 45, further comprising at least one reflective material for reflecting light radiant energy.

*52. A polymerizable isolation barrier for isolating a dental substrate to confine a dental treatment composition to an area defined by the isolation barrier, the polymerizable isolation barrier comprising:*

*at least one polymerizable material;*

*at least one curing agent for curing the at least one polymerizable material; and*

*at least one organic polymerization strength reducer, different than the at least one polymerizable material, for reducing strength of the polymerizable isolation barrier.*

*53. A polymerizable isolation barrier according to claim 52, wherein the polymerizable material comprises at least one component selected from the group consisting of alkylmethacrylates, alkylhydroxymethacrylates, alkylaminomethacrylates, and derivatives thereof.*

*54. A polymerizable isolation barrier according to claim 52, wherein the polymerizable material comprises at least one component selected from the group consisting of triethylene glycol dimethacrylate, polyethylene glycol dimethacrylate, butane di-ol dimethacrylate, 2-hydroxyethyl methacrylate, glycerol dimethacrylate, bis-GMA, and derivatives thereof.*

*55. A polymerizable isolation barrier according to claim 52, wherein the polymerizable material comprises at least one component selected from the group consisting of urethane dimethacrylate and derivatives of urethane dimethacrylate.*

*56. A polymerizable isolation barrier according to claim 52, wherein the at least one polymerizable material comprises at least one monomer that includes a chain of nonreactive units and a reactive unit on each side of the chain.*

*57. A polymerizable isolation barrier according to claim 52, wherein the at least one polymerizable material comprises at least one monomer that has begun to polymerize and that is further polymerizable.*

*58. A polymerizable isolation barrier according to claim 57, wherein the at least one monomer that has begun to polymerize and that is further polymerizable comprises at least one component selected from the group consisting of alkylmethacrylates, alkylhydroxymethacrylates, alkylaminomethacrylates, and derivatives thereof.*

*59. A polymerizable isolation barrier according to claim 57, wherein the at least one monomer that has begun to polymerize and that is further polymerizable comprises at least one component selected from the group consisting of triethylene glycol dimethacrylate, polyethylene glycol dimethacrylate, butane di-ol dimethacrylate, 2-hydroxyethyl methacrylate, glycerol dimethacrylate, bis-GMA, and derivatives thereof.*

*60. A polymerizable isolation barrier according to claim 57, wherein the at least one monomer that has begun to polymerize and that is further polymerizable comprises at least one component selected from the group consisting of urethane dimethacrylate and derivatives of urethane dimethacrylate.*

*61. A polymerizable isolation barrier according to claim 52, wherein the polymerizable material is included in a concentration from about 50% to about 99% by weight of the polymerizable isolation barrier.*

*62. A polymerizable isolation barrier according to claim 52, wherein the organic polymerization strength reducer comprises at least one alcohol.*

*63. A polymerizable isolation barrier according to claim 62, wherein the alcohol comprises at least one of cetyl alcohol or stearyl alcohol.*

*64. A polymerizable isolation barrier according to claim 52, wherein the organic polymerization strength reducer comprises at least one polyol.*

*65. A polymerizable isolation barrier according to claim 64, wherein the polyol comprises at least one of polyethylene glycol, polypropylene glycol, or propylene glycol.*

*66. A polymerizable isolation barrier according to claim 52, wherein the organic polymerization strength reducer comprises at least one oil.*

*67. A polymerizable isolation barrier according to claim 66, wherein the oil comprises mineral oil.*

*68. A polymerizable isolation barrier according to claim 52, wherein the organic polymerization strength reducer is included in a concentration from about 1% to about 30% by weight of the polymerizable isolation barrier.*

*69. A polymerizable isolation barrier according to claim 52, wherein the organic polymerization strength reducer is in sufficient concentration to lower the ability of the polymerizable material to polymerize.*

*70. A polymerizable isolation barrier according to claim 52, wherein the organic polymerization strength reducer is in sufficient concentration to facilitate removal of a polymerized isolation barrier from a dental substrate by hand or by a dental tool.*

*71. A polymerizable isolation barrier according to claim 52, further comprising at least one tissue adherence accentuator selected from the group consisting of gums, xanthan gum, guar gum, tragacanth gum, cellulose materials, ethyl cellulose, hydroxypropylmethyl cellulose, high molecular weight polyols, polyethylene glycol having a molecular weight of at least 600, polypropylene glycol having a molecular weight of at least 600, polysiloxanes, carboxypolymethylene, and water-soluble polyethylene oxides.*

*72. A polymerizable isolation barrier according to claim 71, wherein the tissue adherence accentuator is included in a concentration from about 0.01% to about 9% by weight of the polymerizable isolation barrier.*

*73. A polymerizable isolation barrier according to claim 52, further comprising at least one reflective material for reflecting light radiant energy selected from the group consisting of metals, gold flake, aluminum flake, titanium flake, metal oxides, aluminum oxide, titanium dioxide, precipitated silica, ceria, thoria, and mica.*

*74. A polymerizable isolation barrier according to claim 73, wherein the reflective material is included in a concentration from about 1% to about 50% by weight of the polymerizable isolation barrier.*

*75. A polymerizable isolation barrier according to claim 52, wherein the curing agent comprises a light curing agent that induces the polymerizable material to cross link upon exposure to light radiant energy.*

*76. A polymerizable isolation barrier according to claim 52, wherein the polymerizable isolation barrier is at least one of a paste or gel that is able to be expressed from a dental syringe.*

*77. A polymerizable isolation barrier according to claim 52, wherein the polymerizable isolation barrier comprises at least one of a roll or tape of a curable putty.*

*78. A polymerizable isolation barrier for isolating a dental substrate to confine a dental treatment composition to an area defined by the isolation barrier, the polymerizable isolation barrier comprising:*

*at least one polymerizable material comprising at least one of urethane dimethacrylate or a derivative of urethane dimethacrylate;*

*at least one curing agent for the at least one polymerizable material; and*

*at least one organic polymerization strength reducer, different than the at least one polymerizable material, for reducing strength of the polymerizable isolation barrier.*

*79. A polymerizable isolation barrier according to claim 78, wherein the organic polymerization strength reducer comprises at least one component selected from the group consisting of alcohols, cetyl alcohol, stearyl alcohol, polyols, polyethylene glycol, polypropylene glycol, propylene glycol, oils, and mineral oil.*

*80. A polymerizable isolation barrier according to claim 78, further comprising at least one reflective material for reflecting light radiant energy selected from the group consisting of metals, gold flake, aluminum flake, titanium flake, metal oxides, aluminum oxide, titanium dioxide, precipitated silica, ceria, thoria, and mica.*

*81. A method of making a polymerizable isolation barrier used in isolating a dental substrate to confine a dental treatment composition to an area defined by the isolation barrier, the method comprising:*

*mixing together at least one monomer, at least one curing agent for curing the at least one monomer, and at least one organic polymerization strength reducer for reducing strength of the polymerizable isolation barrier; and*

*partially polymerizing at least a portion of the at least one monomer to yield a polymerizable isolation barrier comprising at least one partially polymerized monomer that is further polymerizable.*

*82. A method of making a polymerizable isolation barrier according to claim 81, wherein the polymerizable isolation barrier is partially polymerized after being applied to oral tissue within a patient's mouth.*

*83. A method of making a polymerizable isolation barrier according to claim 81, wherein the monomer that is partially polymerized comprises at least one of an alkylmethacrylate, an alkylhydroxymethacrylate, or an alkylaminomethacrylate.*

*84. A method of making a polymerizable isolation barrier according to claim 81, wherein the monomer that is partially polymerized comprises at least one component selected from the group consisting of triethylene glycol dimethacrylate, polyethylene glycol dimethacrylate, butane di-ol dimethacrylate, 2-hydroxyethyl methacrylate, glycerol dimethacrylate, bis-GMA, and urethane dimethacrylate.*

*85. A method of making a polymerizable isolation barrier according to claim 81, wherein the organic polymerization strength reducer comprises at least one component selected from the group consisting of alcohols, cetyl alcohol, stearyl alcohol, polyols, polyethylene glycol, polypropylene glycol, propylene glycol, oils, and mineral oil.*

*86. A method of making a polymerizable isolation barrier according to claim 81, wherein the polymerizable isolation barrier further comprises at least one of a tissue adherence accentuator or a reflective material for reflecting light radiant energy.*

*87. A method of isolating hard dental tissue and to contain a dental treatment composition to a defined area comprising:*

*providing a polymerizable isolation barrier composition comprising at least one polymerizable material, at least one curing agent for curing the at least one polymerizable material, and at least one organic polymerization strength reducer for reducing strength of the polymerizable isolation barrier;*

*delivering the polymerizable isolation barrier composition onto an oral tissue surface to isolate hard dental tissue;*

*treating the polymerizable isolation barrier composition with light radiant energy to polymerize at last a portion of the at least one polymerizable material;*

*applying a dental treatment composition to the defined area; and*

*removing the isolation barrier from the dental substrate.*

*88. A method according to claim 87, wherein the isolation barrier is removed using a dental tool.*

*89. A method according to claim 87, wherein the isolation barrier is removed by hand.*

* * * * *

UNITED STATES PATENT AND TRADEMARK OFFICE

CERTIFICATE OF CORRECTION

PATENT NO. : RE 38,721 E
DATED : April 12, 2005
INVENTOR(S) : Steven D. Jensen and Dan E. Fischer It is certified that error appears in the above-identified patent and that said Letters Patent is hereby corrected as shown below:

Column 2,
Line 40, change “resulting” to -- resultantly --.
Line 54, change “necessary be” to -- be necessary --.
Line 55, change “tools which the” to -- tools, which --.
Line 55, after “force” insert -- , --.

Column 8,
Line 5, before “integral unit” insert -- an --.
Line 10, change “preferable” to -- preferably --.

Column 9,
Line 50, change “during” to -- on the --.

Column 10,
Line 38, change “32” to -- 12 --.

Column 13,
Line 50, change “illustrated” to -- illustrative --.

Column 15,
Line 23, change “polsiloxanes” to -- polysiloxanes --.

Signed and Sealed this

Eighteenth Day of October, 2005

JON W. DUDAS
*Director of the United States Patent and Trademark Office*